(12) United States Patent
Li

(10) Patent No.: US 9,062,023 B2
(45) Date of Patent: Jun. 23, 2015

(54) HETEROCYCLE COMPOUNDS AND USES THEREOF

(75) Inventor: Peng Li, New York, NY (US)

(73) Assignee: Intra-Cellular Therapies, Inc., New York, NY (US)

( * ) Notice: Subject to any disclaimer, the term of this patent is extended or adjusted under 35 U.S.C. 154(b) by 1045 days.

(21) Appl. No.: 12/663,224

(22) PCT Filed: Jun. 6, 2008

(86) PCT No.: PCT/US2008/007167
§ 371 (c)(1),
(2), (4) Date: Dec. 4, 2009

(87) PCT Pub. No.: WO2008/153974
PCT Pub. Date: Dec. 18, 2008

(65) Prior Publication Data
US 2010/0184778 A1 Jul. 22, 2010

Related U.S. Application Data

(60) Provisional application No. 60/933,782, filed on Jun. 7, 2007.

(51) Int. Cl.
| A01N 43/54 | (2006.01) |
|---|---|
| A61K 31/505 | (2006.01) |
| C07D 403/00 | (2006.01) |
| C07D 239/02 | (2006.01) |
| C07D 401/04 | (2006.01) |
| C07D 401/12 | (2006.01) |
| C07D 401/14 | (2006.01) |

(52) U.S. Cl.
CPC ............ *C07D 401/04* (2013.01); *C07D 401/12* (2013.01); *C07D 401/14* (2013.01)

(58) Field of Classification Search
USPC .................................. 514/275; 544/295, 332
See application file for complete search history.

(56) References Cited

U.S. PATENT DOCUMENTS

| 5,521,184 | A | 5/1996 | Zimmermann |
| 6,596,746 | B1 | 7/2003 | Das et al. |
| 2004/0028673 | A1 | 2/2004 | Netzer et al. |
| 2004/0176395 | A1 | 9/2004 | Flynn et al. |
| 2006/0293340 | A1 | 12/2006 | Batt et al. |
| 2008/0312251 | A1* | 12/2008 | Sun et al. .................. 514/252.18 |
| 2010/0120787 | A1 | 5/2010 | Sutcliffe et al. |
| 2010/0173924 | A1 | 7/2010 | Li |

FOREIGN PATENT DOCUMENTS

| CA | 2 602 738 | * 12/2005 | ........... C07D 239/42 |
| CN | 1972917 | * 8/2010 | ........... C07D 403/02 |
| EP | 0 564 409 | 1/2001 | |
| EP | 1 533 304 | 5/2005 | |
| EP | 1 840 122 | * 10/2007 | ........... C07D 239/42 |
| WO | WO 03/057165 | 7/2003 | |
| WO | WO 03/062220 | 7/2003 | |
| WO | WO 2004/005281 | 1/2004 | |
| WO | WO 2004/110452 | 12/2004 | |
| WO | WO 2005/039586 | 5/2005 | |
| WO | WO 2005/072826 | 11/2005 | |
| WO | WO 2006/021458 | 3/2006 | |
| WO | WO 2006/069525 | * 7/2006 | ........... C07D 239/42 |

OTHER PUBLICATIONS

Nurden, Platelets, Inflammation and Tissue Regeneration, Thrombosis and Haemostasis Supplement, S13-S33 (2011).*
Appels et al, "Quantitative analysis of the farnesyl transferase inhibitor lonafarib (Sarasar™, SCH66336) in human plasma using high performance liquid chromatography coupled with tandem mass spectrometry" Rapid Commun. Mass Spectrom (2005) 19: 2187-2192.
Netzer et al, "Gleevec inhibits β-amyloid production but not Notch cleavage"Proc. Nat'l. Acad. Sci. (2003) 100(21) 12444-12449.
Plant et al, "The production of amyloid beta peptide is a critical requirement for the viability of central neurons" J. Neurosci. (2003) 23(13): 5631-5535.
Yadim, M. "The path from anti Parkinson drug selegiline and rasagiline to multifunctional neuroprotective anti Alzheimer drugs ladostigil and m30" Curr. Alzh.Res. (2006) 3 (5) 541-50.
Zhao et al., "Specific method for determination of gefitinib in human plasma, mouse plasma and tissues using high performance liquid chromatography coupled to tandem mass spectrometry" J. Chromatogr. B. Analyt. Technol. Biomed Life Sci. (2005) 819: 73-80.
Zimmerman et al, "Potent and Selective inhibitors of the ABL-Kinase: phenylamino-pyrimidine (PAP) derivatives" Bioorganic & Medicinal Chem. Lett. (1997), 7(2): 187-192.

(Continued)

Primary Examiner — Erich A Leeser
(74) Attorney, Agent, or Firm — Hoxie & Associates, LLC

(57) ABSTRACT

The invention relates to chemical compounds, or pharmaceutically acceptable salts thereof of the formula (Q) or (I), which penetrate the blood-brain barrier, inhibit the formation and accumulation of beta-amyloid, and are useful in the treatment of neurodegenerative diseases, particularly Alzheimer's disease. Further, the compounds of the present invention inhibit certain kinases, thereby being useful for the treatment of cancers of the central nervous system.

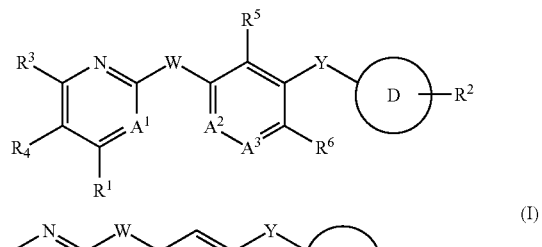

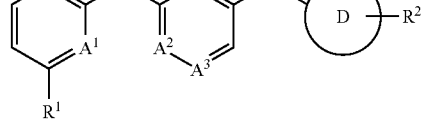

43 Claims, No Drawings

(56) References Cited

OTHER PUBLICATIONS

International Search Report and Written Opinion of the International Searching Authority for International Application No. PCT/US2008/007167 dated Aug. 18, 2008.

Office Action from the European Patent Office for EP Application No. 08768240.7 dated Sep. 5, 2011.
Office Action from the European Patent Office for EP Application No. 08768240.7 dated Mar. 9, 2012.
Supplementary Search Report from the European Patent Office for EP Application No. 08768240.7 dated May 7, 2010.

* cited by examiner

HETEROCYCLE COMPOUNDS AND USES THEREOF

CROSS REFERENCE TO RELATED APPLICATIONS

This application is a US filing under 35 USC 371 of International Application No. PCT/US2008/007167 filed on Jun. 6, 2008, which claims the benefit of U.S. Provisional Application 60/933,732 filed on Jun. 7, 2007 the contents of each of which are incorporated herein by reference.

FIELD OF THE INVENTION

The present invention relates to novel heterocycles, their pharmaceutical compositions and methods of use. In addition, the present invention relates to therapeutic methods that penetrate the blood-brain barrier and inhibit the formation and accumulation of beta-amyloid. Accordingly, the compounds and compositions of the present invention are useful in the treatment of neurodegenerative diseases, particularly Alzheimer's disease. Further, the compounds of the present invention inhibit certain kinases, thereby being useful for the treatment of cancers of the central nervous system.

BACKGROUND OF THE INVENTION

Without being bound to theory, it is believed that the pathology of Alzheimer's disease ("AD") involves amyloid-β ("Aβ") peptides, which are metabolites of β-amyloid precursor protein (Alzheimer's disease-associated precursor protein or "APP"), and are believed to be major pathological determinants of AD. These peptides consist mainly of 40 to 42 amino acids, Aβ1-40 ("Aβ40") and Aβ1-42 ("Aβ42"), respectively. Aβ40 and Aβ42 are generated by two enzymatic cleavages occurring close to the C-terminus of APP. The enzymes responsible for the cleavage, β-secretase and γ-secretase, generate the N- and C-termini of Aβ, respectively. The amino terminus of Aβ is formed by β-secretase cleavage between methionine residue 596 and aspartate residue 597 of APP (numbering based o APP 695 isoform). γ-secretase cleaves at varying positions 38-, 40- or 43-residues C-terminal of this β-secretase cleavage product to release the Aβ peptides. A third enzyme, α-secretase, cleaves the precursor protein between the Aβ- and γ-cleavage sites, thus precluding Aβ production and releasing an approximately 3 kDa peptide known as P3, which is non-pathological. Both β- and α-secretase cleavage also result in soluble, secreted-terminal fragments of APP, known as sAPPβ and sAPPα, respectively. The sAPPα fragment has been suggested to be neuroprotective. These secretases may also be involved in the processing of other important proteins. For example, γ-secretase also cleaves Notch-1 protein.

A drug which selectively inhibits Aβ formation and/or accumulation is thus of potential interest for the treatment, management and prevention of Alzheimer's disease. To maximize utility, however, it is also desirable that it can be readily delivered to relevant site of action in the brain. Brain is protected from chemical insult by a selective barrier, referred to as the blood-brain barrier ("BBB"), that many drug-like compounds are unable to penetrate.

International Patent Publication No. WO 03/057165 discloses that certain previously known inhibitors of tyrosine kinases are useful to inhibit the production of and accumulation of Aβ. Such compounds included those described in U.S. Pat. No. 5,521,184, which includes imatinib. Netzer et al., *Proc Natl Acad Sci.*, 100(21):12444-9 (2003) showed that imatinib inhibits production of Aβ without affecting γ-secretase cleavage of Notch-1 and without unacceptable toxicity to the neurons. A major disadvantage with using imatinib for the treatment or prevention of Alzheimer's disease, however, is that penetration of this compound across the BBB is poor because imatinib is actively pumped out of the brain by a P-glycoprotein system, thereby preventing high concentrations of the compound from accumulating in the brain. Accordingly, imatinib is generally not used for the treatment of cancers of the central nervous system.

International Patent Publication No. WO 05/072826 describes compositions and methods of use for tyrosine kinase inhibitors to treat pathogenic infection. J. Zimmermann et al., *Bioorganic & Medicinal Chem. Lett.*, 7(2):187-192 describes potent and selective inhibitors of the ABL-kinase: phenylamino-pyrimidine (PAP) derivatives. International Patent Publication No. EP 1 533 304 describes amide derivatives. International Patent Publication No. WO 04/005281 describes inhibitors of tyrosine kinases. International Patent Publication No. WO 05/039586 describes the use of pyridinyl-pyrimidinylamino-benzamide derivatives for the treatment of amyloid related disorders. U.S. Pat. No. 5,521,184 describes pyrimidine derivatives and processes for the preparation thereof. International Patent Publication No. WO 04/110452 describes substituted phenyl compounds.

SUMMARY OF THE INVENTION

The present invention is directed to compounds of formula (Q):

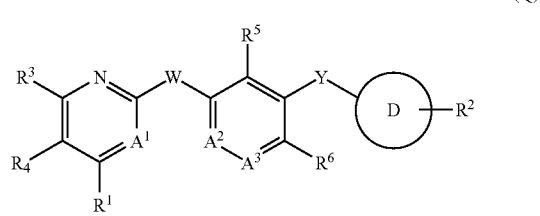

Formula (Q)

in free or salt form, which penetrate the blood-brain barrier, inhibit the formation and accumulation of beta-amyloid, and are useful in the treatment of neurodegenerative diseases, particularly Alzheimer's disease. Further, the compounds of the present invention inhibit certain kinases, thereby being useful for the treatment of cancers of the central nervous system.

The present invention is also directed to compounds of formula (I):

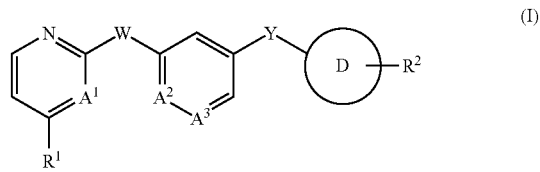

(I)

which penetrate the blood-brain barrier, inhibit the formation and accumulation of beta-amyloid, and are useful in the treatment of neurodegenerative diseases, particularly Alzheimer's disease. Further, the compounds of the present invention inhibit certain kinases, thereby being useful for the treatment of cancers of the central nervous system.

DETAILED DESCRIPTION OF THE INVENTION

In one aspect, the compounds of the present invention are presented by

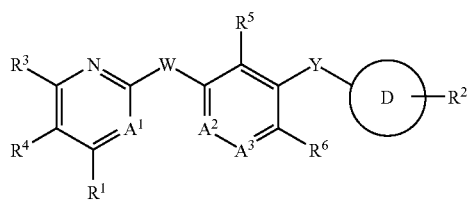

Formula (Q)

in free or salt form, wherein:

$A^1$ is —C($R^7$)— or —N—;

$A^2$ and $A^3$ are independently —C— or —N—, wherein at least one of $A^2$ and $A^3$ must be N; and wherein when $A^2$ is —C—, it optionally is substituted with $R^8$;

W is —O— or —N($C_{0-6}$alkyl)-;

Y is —NHCO—, —CONH—, —NHSO$_2$—, —NHCONH—, or —NHCH$_2$—;

D is a 5 or 6 membered aryl, hetaryl or hetcyclic ring having at least one N, S, or O ring atom, or a C ring atom forming an oxo (C=O) moiety;

$R^1$ is $C_{1-6}$alkyl, aryl, or hetaryl; optionally substituted except at the ortho position of the aryl or hetaryl with 1-6 halo, $C_{1-6}$alkoxy, $C_{1-6}$alkyl, or trifluoromethyl substituents; wherein the ortho aryl or hetaryl position is unsubstituted;

$R^2$ is $C_{0-6}$alkyl, $C_{3-7}$cycloalkyl, aryl, hetaryl, aryl($C_{1-4}$alkyl)-, hetcyclyl($C_{0-4}$alkyl)-, or —$C_{0-6}$alkyl-N($C_{0-6}$alkyl)($C_{0-6}$alkyl), optionally substituted with $C_{1-6}$alkyl; and $R^3$, $R^4$, $R^5$, $R^6$, $R^7$ and $R^8$ are independently selected from hydrogen, halo, $C_{1-4}$alkyl (e.g., methyl), $C_{1-4}$alkoxyl (e.g., methoxy), and halo $C_{1-4}$alkyl (e.g., trifluoromethyl).

In another aspect, the compounds of the present invention are represented by formula (I):

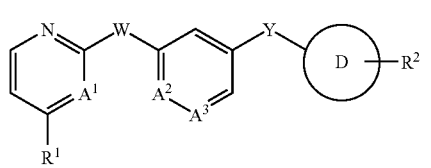

(I)

in free or salt form, wherein:

$A^1$ is CH or N;

$A^2$ and $A^3$ are independently CH or N, wherein at least one of $A^2$ and $A^3$ must be N; and wherein when $A^2$ is C, it optionally is substituted with halo, methyl, methoxy, or trifluoromethyl;

W is —O— or —N($C_{0-6}$alkyl)-;

Y is —NHCO—, —CONH—, —NHSO$_2$—, —NHCONH—, or —NHCH$_2$—;

D is a 5 or 6 membered aryl, hetaryl or hetcyclic ring having at least one N, S, or O ring atom, or a C ring atom forming an oxo (C=O) moiety;

$R^1$ is $C_{1-6}$alkyl, aryl, or hetaryl; optionally substituted except at the ortho position of the aryl or hetaryl with 1-6 halo, $C_{1-6}$alkoxy, $C_{1-6}$alkyl, or trifluoromethyl substituents; wherein the ortho aryl or hetaryl position is unsubstituted; and $R^2$ is $C_{0-6}$alkyl, $C_{3-7}$cycloalkyl, aryl, hetaryl, aryl($C_{1-4}$alkyl)-, hetcyclyl($C_{0-4}$alkyl)-, or —$C_{0-6}$alkyl-N($C_{0-6}$alkyl)($C_{0-6}$alkyl), optionally substituted with $C_{1-6}$alkyl.

In one aspect, the compounds of the present invention are represented by Formula I in free or salt form, wherein W is —O— and the other variables are as defined above for Formula I.

In an embodiment of this aspect, the compounds of the present invention are represented by Formula I in free or salt form, wherein W is —O—; Y is —NHCO—; and the other variables are as defined above for Formula I.

In an embodiment of this aspect, the compounds of the present invention are represented by Formula I in free or salt form, wherein W is —O—; Y is —NHCO—; $A^2$ is N; $A^3$ is CH optionally substituted with halo, methyl, methoxy, or trifluoromethyl; and the other variables are as defined above for Formula I.

In an embodiment of this aspect, the compounds of the present invention are represented by Formula I in free or salt form, wherein W is —O—; Y is —NHCO—; $A^1$ is CH; $A^2$ is N; $A^3$ is CH optionally substituted with halo, methyl, methoxy, or trifluoromethyl; and the other variables are as defined above for Formula I.

In an embodiment of this aspect, the compounds of the present invention are represented by Formula I in free or salt form, wherein W is —O—; Y is —NHCO—; $A^1$ is N; $A^2$ is N; $A^3$ is CH optionally substituted with halo, methyl, methoxy, or trifluoromethyl; and the other variables are as defined above for Formula I.

In an embodiment of this aspect, the compounds of the present invention are represented by Formula I in free or salt form, wherein W is —O—; Y is —NHCO—; $A^3$ is N; $A^2$ is CH optionally substituted with halo, methyl, methoxy, or trifluoromethyl; and the other variables are as defined above for Formula I.

In an embodiment of this aspect, the compounds of the present invention are represented by Formula I in free or salt form, wherein W is —O—; Y is —NHCO—; $A^1$ is CH; $A^3$ is N; $A^2$ is CH optionally substituted with halo, methyl, methoxy, or trifluoromethyl; and the other variables are as defined above for Formula I.

In an embodiment of this aspect, the compounds of the present invention are represented by Formula I in free or salt form, wherein W is —O—; Y is —NHCO—; $A^1$ is N; $A^3$ is N; $A^2$ is CH optionally substituted with halo, methyl, methoxy, or trifluoromethyl; and the other variables are as defined above for Formula I.

In another embodiment of this aspect, the compounds of the present invention are represented by Formula I in free or salt form, wherein W is —O—; Y is —CONH—; and the other variables are as defined above for Formula I.

In another embodiment of this aspect, the compounds of the present invention are represented by Formula I in free or salt form, wherein W is —O—; Y is —CONH—; $A^2$ is N; $A^3$ is CH optionally substituted with halo, methyl, methoxy, or trifluoromethyl; and the other variables are as defined above for Formula I.

In another embodiment of this aspect, the compounds of the present invention are represented by Formula I in free or salt form, wherein W is —O—; Y is —CONH—; $A^1$ is CH; $A^2$ is N; $A^3$ is CH optionally substituted with halo, methyl, methoxy, or trifluoromethyl; and the other variables are as defined above for Formula I.

In another embodiment of this aspect, the compounds of the present invention are represented by Formula I in free or salt form, wherein W is —O—; Y is —CONH—; $A^1$ is N; $A^2$ is N; $A^3$ is CH optionally substituted with halo, methyl, methoxy, or trifluoromethyl; and the other variables are as defined above for Formula I.

In another embodiment of this aspect, the compounds of the present invention are represented by Formula I in free or salt form, wherein W is —O—; Y is —CONH—; $A^3$ is N; $A^2$ is CH optionally substituted with halo, methyl, methoxy, or trifluoromethyl; and the other variables are as defined above for Formula I.

In another embodiment of this aspect, the compounds of the present invention are represented by Formula I in free or salt form, wherein W is —O—; Y is —CONH—; $A^1$ is CH; $A^3$ is N; $A^2$ is CH optionally substituted with halo, methyl, methoxy, or trifluoromethyl; and the other variables are as defined above for Formula I.

In another embodiment of this aspect, the compounds of the present invention are represented by Formula I in free or salt form, wherein W is —O—; Y is —CONH—; $A^1$ is N; $A^3$ is N; $A^2$ is CH optionally substituted with halo, methyl, methoxy, or trifluoromethyl; and the other variables are as defined above for Formula I.

In still another embodiment of this aspect, the compounds of the present invention are represented by Formula I in free or salt form, wherein W is —O—; Y is —NHSO$_2$—; and the other variables are as defined above for Formula I.

In still another embodiment of this aspect, the compounds of the present invention are represented by Formula I in free or salt form, wherein W is —O—; Y is —NHSO$_2$—; $A^2$ is N; $A^3$ is CH optionally substituted with halo, methyl, methoxy, or trifluoromethyl; and the other variables are as defined above for Formula I.

In still another embodiment of this aspect, the compounds of the present invention are represented by Formula I in free or salt form, wherein W is —O—; Y is —NHSO$_2$—; $A^1$ is CH; $A^2$ is N; $A^3$ is CH optionally substituted with halo, methyl, methoxy, or trifluoromethyl; and the other variables are as defined above for Formula I.

In still another embodiment of this aspect, the compounds of the present invention are represented by Formula I in free or salt form, wherein W is —O—; Y is —NHSO$_2$—; $A^1$ is N; $A^2$ is N; $A^3$ is CH optionally substituted with halo, methyl, methoxy, or trifluoromethyl; and the other variables are as defined above for Formula I.

In still another embodiment of this aspect, the compounds of the present invention are represented by Formula I in free or salt form, wherein W is —O—; Y is —NHSO$_2$—; $A^3$ is N; $A^2$ is CH optionally substituted with halo, methyl, methoxy, or trifluoromethyl; and the other variables are as defined above for Formula I.

In still another embodiment of this aspect, the compounds of the present invention are represented by Formula I in free or salt form, wherein W is —O—; Y is —NHSO$_2$—; $A^1$ is CH; $A^3$ is N; $A^2$ is CH optionally substituted with halo, methyl, methoxy, or trifluoromethyl; and the other variables are as defined above for Formula I.

In still another embodiment of this aspect, the compounds of the present invention are represented by Formula I in free or salt form, wherein W is —O—; Y is —NHSO$_2$—; $A^1$ is N; $A^3$ is N; $A^2$ is CH optionally substituted with halo, methyl, methoxy, or trifluoromethyl; and the other variables are as defined above for Formula I.

In another embodiment of this aspect, the compounds of the present invention are represented by Formula I in free or salt form, wherein W is —O—; Y is —NHCONH—; and the other variables are as defined above for Formula I.

In another embodiment of this aspect, the compounds of the present invention are represented by Formula I in free or salt form, wherein W is —O—; Y is —NHCONH—; $A^2$ is N; $A^3$ is CH optionally substituted with halo, methyl, methoxy, or trifluoromethyl; and the other variables are as defined above for Formula I.

In another embodiment of this aspect, the compounds of the present invention are represented by Formula I in free or salt form, wherein W is —O—; Y is —NHCONH—; $A^2$ is N; $A^1$ is CH; $A^3$ is CH optionally substituted with halo, methyl, methoxy, or trifluoromethyl; and the other variables are as defined above for Formula I.

In another embodiment of this aspect, the compounds of the present invention are represented by Formula I in free or salt form, wherein W is —O—; Y is —NHCONH—; $A^2$ is N; $A^1$ is N; $A^3$ is CH optionally substituted with halo, methyl, methoxy, or trifluoromethyl; and the other variables are as defined above for Formula I.

In another embodiment of this aspect, the compounds of the present invention are represented by Formula I in free or salt form, wherein W is —O—; Y is —NHCONH—; $A^3$ is N; $A^2$ is CH optionally substituted with halo, methyl, methoxy, or trifluoromethyl; and the other variables are as defined above for Formula I.

In another embodiment of this aspect, the compounds of the present invention are represented by Formula I in free or salt form, wherein W is —O—; Y is —NHCONH—; $A^1$ is CH; $A^3$ is N; $A^2$ is CH optionally substituted with halo, methyl, methoxy, or trifluoromethyl; and the other variables are as defined above for Formula I.

In another embodiment of this aspect, the compounds of the present invention are represented by Formula I in free or salt form, wherein W is —O—; Y is —NHCONH—; $A^1$ is N; $A^3$ is N; $A^2$ is CH optionally substituted with halo, methyl, methoxy, or trifluoromethyl; and the other variables are as defined above for Formula I.

In yet another embodiment of this aspect, the compounds of the present invention are represented by Formula I in free or salt form, wherein W is —O—; Y is —NHCH$_2$—; and the other variables are as defined above for Formula I.

In yet another embodiment of this aspect, the compounds of the present invention are represented by Formula I in free or salt form, wherein W is —O—; Y is —NHCH$_2$—; $A^2$ is N; $A^3$ is CH optionally substituted with halo, methyl, methoxy, or trifluoromethyl; and the other variables are as defined above for Formula I.

In yet another embodiment of this aspect, the compounds of the present invention are represented by Formula I in free or salt form, wherein W is —O—; Y is —NHCH$_2$—; $A^1$ is CH; $A^2$ is N; $A^3$ is CH optionally substituted with halo, methyl, methoxy, or trifluoromethyl; and the other variables are as defined above for Formula I.

In yet another embodiment of this aspect, the compounds of the present invention are represented by Formula I in free or salt form, wherein W is —O—; Y is —NHCH$_2$—; $A^1$ is N; $A^2$ is N; $A^3$ is CH optionally substituted with halo, methyl, methoxy, or trifluoromethyl; and the other variables are as defined above for Formula I.

In yet another embodiment of this aspect, the compounds of the present invention are represented by Formula I in free or salt form, wherein W is —O—; Y is —NHCH$_2$—; $A^3$ is N; $A^2$ is CH optionally substituted with halo, methyl, methoxy, or trifluoromethyl; and the other variables are as defined above for Formula I.

In yet another embodiment of this aspect, the compounds of the present invention are represented by Formula I in free or salt form, wherein W is —O—; Y is —NHCH$_2$—; $A^1$ is CH; $A^3$ is N; $A^2$ is CH optionally substituted with halo, methyl, methoxy, or trifluoromethyl; and the other variables are as defined above for Formula I.

In yet another embodiment of this aspect, the compounds of the present invention are represented by Formula I in free or salt form, wherein W is —O—; Y is —NHCH$_2$—; A$^1$ is N; A$^3$ is N; A$^2$ is CH optionally substituted with halo, methyl, methoxy, or trifluoromethyl; and the other variables are as defined above for Formula I.

In another aspect, the compounds of the present invention are represented by Formula I in free or salt form, wherein W is —N(C$_{0-6}$alkyl)- and the other variables are as defined above for Formula I.

In an embodiment of this aspect, the compounds of the present invention are represented by Formula I in free or salt form, wherein W is —N(C$_{0-6}$alkyl)-; Y is —NHCO—; and the other variables are as defined above for Formula I.

In an embodiment of this aspect, the compounds of the present invention are represented by Formula I in free or salt form, wherein W is —N(C$_{0-6}$alkyl)-; Y is —NHCO—; A$^2$ is N; A$^3$ is CH optionally substituted with halo, methyl, methoxy, or trifluoromethyl; and the other variables are as defined above for Formula I.

In an embodiment of this aspect, the compounds of the present invention are represented by Formula I in free or salt form, wherein W is —N(C$_{0-6}$alkyl)-; Y is —NHCO—; A$^1$ is CH; A$^2$ is N; A$^3$ is CH optionally substituted with halo, methyl, methoxy, or trifluoromethyl; and the other variables are as defined above for Formula I.

In an embodiment of this aspect, the compounds of the present invention are represented by Formula I in free or salt form, wherein W is —N(C$_{0-6}$alkyl)-; Y is —NHCO—; A$^1$ is N; A$^2$ is N; A$^3$ is CH optionally substituted with halo, methyl, methoxy, or trifluoromethyl; and the other variables are as defined above for Formula I.

In an embodiment of this aspect, the compounds of the present invention are represented by Formula I in free or salt form, wherein W is —N(C$_{0-6}$alkyl)-; Y is —NHCO—; A$^3$ is N; A$^2$ is CH optionally substituted with halo, methyl, methoxy, or trifluoromethyl; and the other variables are as defined above for Formula I.

In an embodiment of this aspect, the compounds of the present invention are represented by Formula I in free or salt form, wherein W is —N(C$_{0-6}$alkyl)-; Y is —NHCO—; A$^1$ is CH; A$^3$ is N; A$^2$ is CH optionally substituted with halo, methyl, methoxy, or trifluoromethyl; and the other variables are as defined above for Formula I.

In an embodiment of this aspect, the compounds of the present invention are represented by Formula I in free or salt form, wherein W is —N(C$_{0-6}$alkyl)-; Y is —NHCO—; A$^1$ is N; A$^3$ is N; A$^2$ is CH optionally substituted with halo, methyl, methoxy, or trifluoromethyl; and the other variables are as defined above for Formula I.

In yet another embodiment, the compounds of the present invention are represented by Formula I in free or salt form, wherein W is —N(C$_{0-6}$alkyl)-; Y is —CONH—; and the other variables are as defined above for Formula I.

In yet another embodiment, the compounds of the present invention are represented by Formula I in free or salt form, wherein W is —N(C$_{0-6}$alkyl)-; Y is —CONH—; A$^2$ is N; A$^3$ is CH optionally substituted with halo, methyl, methoxy, or trifluoromethyl; and the other variables are as defined above for Formula I.

In yet another embodiment, the compounds of the present invention are represented by Formula I in free or salt form, wherein W is —N(C$_{0-6}$alkyl)-; Y is —CONH—; A$^1$ is CH; A$^2$ is N; A$^3$ is CH optionally substituted with halo, methyl, methoxy, or trifluoromethyl; and the other variables are as defined above for Formula I.

In yet another embodiment, the compounds of the present invention are represented by Formula I in free or salt form, wherein W is —N(C$_{0-6}$alkyl)-; Y is —CONH—; A$^1$ is N; A$^2$ is N; A$^3$ is CH optionally substituted with halo, methyl, methoxy, or trifluoromethyl; and the other variables are as defined above for Formula I.

In yet another embodiment, the compounds of the present invention are represented by Formula I in free or salt form, wherein W is —N(C$_{0-6}$alkyl)-; Y is —CONH—; A$^3$ is N; A$^2$ is CH optionally substituted with halo, methyl, methoxy, or trifluoromethyl; and the other variables are as defined above for Formula I.

In yet another embodiment, the compounds of the present invention are represented by Formula I in free or salt form, wherein W is —N(C$_{0-6}$alkyl)-; Y is —CONH—; A$^1$ is CH; A$^3$ is N; A$^2$ is CH optionally substituted with halo, methyl, methoxy, or trifluoromethyl; and the other variables are as defined above for Formula I.

In yet another embodiment, the compounds of the present invention are represented by Formula I in free or salt form, wherein W is —N(C$_{0-6}$alkyl)-; Y is —CONH—; A$^1$ is N; A$^3$ is N; A$^2$ is CH optionally substituted with halo, methyl, methoxy, or trifluoromethyl; and the other variables are as defined above for Formula I.

In still another embodiment of this aspect, the compounds of the present invention are represented by Formula I in free or salt form, wherein W is —N(C$_{0-6}$alkyl)-; Y is —NHSO$_2$—; and the other variables are as defined above for Formula I.

In still another embodiment of this aspect, the compounds of the present invention are represented by Formula I in free or salt form, wherein W is —N(C$_{0-6}$alkyl)-; Y is —NHSO$_2$—; A$^2$ is N; A$^3$ is CH optionally substituted with halo, methyl, methoxy, or trifluoromethyl; and the other variables are as defined above for Formula I.

In still another embodiment of this aspect, the compounds of the present invention are represented by Formula I in free or salt form, wherein W is —N(C$_{0-6}$alkyl)-; Y is —NHSO$_2$—; A$^1$ is CH; A$^2$ is N; A$^3$ is CH optionally substituted with halo, methyl, methoxy, or trifluoromethyl; and the other variables are as defined above for Formula I.

In still another embodiment of this aspect, the compounds of the present invention are represented by Formula I in free or salt form, wherein W is —N(C$_{0-6}$alkyl)-; Y is —NHSO$_2$—; A$^1$ is N; A$^2$ is N; A$^3$ is CH optionally substituted with halo, methyl, methoxy, or trifluoromethyl; and the other variables are as defined above for Formula I.

In still another embodiment of this aspect, the compounds of the present invention are represented by Formula I in free or salt form, wherein W is —N(C$_{0-6}$alkyl)-; Y is —NHSO$_2$—; A$^3$ is N; A$^2$ is CH optionally substituted with halo, methyl, methoxy, or trifluoromethyl; and the other variables are as defined above for Formula I.

In still another embodiment of this aspect, the compounds of the present invention are represented by Formula I in free or salt form, wherein W is —N(C$_{0-6}$alkyl)-; Y is —NHSO$_2$—; A$^1$ is CH; A$^3$ is N; A$^2$ is CH optionally substituted with halo, methyl, methoxy, or trifluoromethyl; and the other variables are as defined above for Formula I.

In still another embodiment of this aspect, the compounds of the present invention are represented by Formula I in free or salt form, wherein W is —N(C$_{0-6}$alkyl)-; Y is —NHSO$_2$—; A$^1$ is N; A$^3$ is N; A$^2$ is CH optionally substituted with halo, methyl, methoxy, or trifluoromethyl; and the other variables are as defined above for Formula I.

In another embodiment, the compounds of the present invention are represented by Formula I in free or salt form, wherein W is —N($C_{0-6}$alkyl)-; Y is —NHCONH—; and the other variables are as defined above for Formula I.

In another embodiment, the compounds of the present invention are represented by Formula I in free or salt form, wherein W is —N($C_{0-6}$alkyl)-; Y is —NHCONH—; $A^2$ is N; $A^3$ is CH optionally substituted with halo, methyl, methoxy, or trifluoromethyl; and the other variables are as defined above for Formula I.

In another embodiment, the compounds of the present invention are represented by Formula I in free or salt form, wherein W is —N($C_{0-6}$alkyl)-; Y is —NHCONH—; $A^1$ is CH; $A^2$ is N; $A^3$ is CH optionally substituted with halo, methyl, methoxy, or trifluoromethyl; and the other variables are as defined above for Formula I.

In another embodiment, the compounds of the present invention are represented by Formula I in free or salt form, wherein W is —N($C_{0-6}$alkyl)-; Y is —NHCONH—; $A^1$ is N; $A^2$ is N; $A^3$ is CH optionally substituted with halo, methyl, methoxy, or trifluoromethyl; and the other variables are as defined above for Formula I.

In another embodiment, the compounds of the present invention are represented by Formula I in free or salt form, wherein W is —N($C_{0-6}$alkyl)-; Y is —NHCONH—; $A^3$ is N; $A^2$ is CH optionally substituted with halo, methyl, methoxy, or trifluoromethyl; and the other variables are as defined above for Formula I.

In another embodiment, the compounds of the present invention are represented by Formula I in free or salt form, wherein W is —N($C_{0-6}$alkyl)-; Y is —NHCONH—; $A^1$ is CH; $A^3$ is N; $A^2$ is CH optionally substituted with halo, methyl, methoxy, or trifluoromethyl; and the other variables are as defined above for Formula I.

In another embodiment, the compounds of the present invention are represented by Formula I in free or salt form, wherein W is —N($C_{0-6}$alkyl)-; Y is —NHCONH—; $A^1$ is N; $A^3$ is N; $A^2$ is CH optionally substituted with halo, methyl, methoxy, or trifluoromethyl; and the other variables are as defined above for Formula I.

In yet another embodiment of this aspect, the compounds of the present invention are represented by Formula I in free or salt form, wherein W is —N($C_{0-6}$alkyl)-; Y is —NHCH$_2$—; and the other variables are as defined above for Formula I.

In yet another embodiment of this aspect, the compounds of the present invention are represented by Formula I in free or salt form, wherein W is —N($C_{0-6}$alkyl)-; Y is —NHCH$_2$—; $A^2$ is N; $A^3$ is CH optionally substituted with halo, methyl, methoxy, or trifluoromethyl; and the other variables are as defined above for Formula I.

In yet another embodiment of this aspect, the compounds of the present invention are represented by Formula I in free or salt form, wherein W is —N($C_{0-6}$alkyl)-; Y is —NHCH$_2$—; $A^1$ is CH; $A^2$ is N; $A^3$ is CH optionally substituted with halo, methyl, methoxy, or trifluoromethyl; and the other variables are as defined above for Formula I.

In yet another embodiment of this aspect, the compounds of the present invention are represented by Formula I in free or salt form, wherein W is —N($C_{0-6}$alkyl)-; Y is —NHCH$_2$—; $A^1$ is N; $A^2$ is N; $A^3$ is CH optionally substituted with halo, methyl, methoxy, or trifluoromethyl; and the other variables are as defined above for Formula I.

In yet another embodiment of this aspect, the compounds of the present invention are represented by Formula I in free or salt form, wherein W is —N($C_{0-6}$alkyl)-; Y is —NHCH$_2$—; $A^3$ is N; $A^2$ is CH optionally substituted with halo, methyl, methoxy, or trifluoromethyl; and the other variables are as defined above for Formula I.

In yet another embodiment of this aspect, the compounds of the present invention are represented by Formula I in free or salt form, wherein W is —N($C_{0-6}$alkyl)-; Y is —NHCH$_2$—; $A^1$ is CH; $A^3$ is N; $A^2$ is CH optionally substituted with halo, methyl, methoxy, or trifluoromethyl; and the other variables are as defined above for Formula I.

In yet another embodiment of this aspect, the compounds of the present invention are represented by Formula I in free or salt form, wherein W is —N($C_{0-6}$alkyl)-; Y is —NHCH$_2$—; $A^1$ is N; $A^3$ is N; $A^2$ is CH optionally substituted with halo, methyl, methoxy, or trifluoromethyl; and the other variables are as defined above for Formula I.

In another aspect, the present invention comprises any of the following compounds:

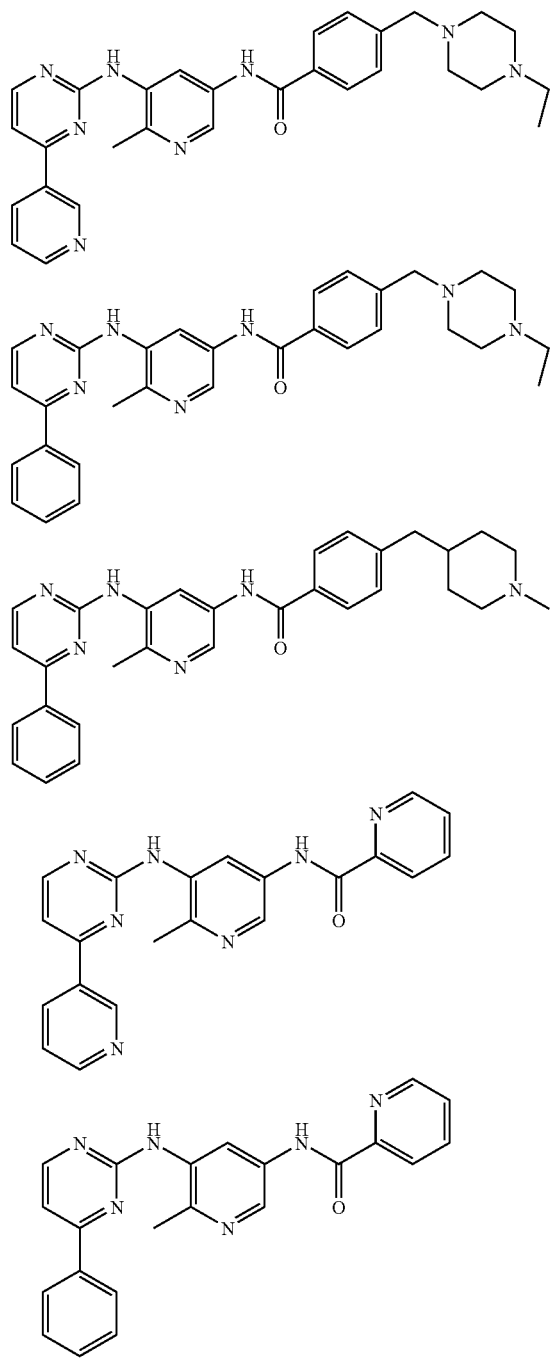

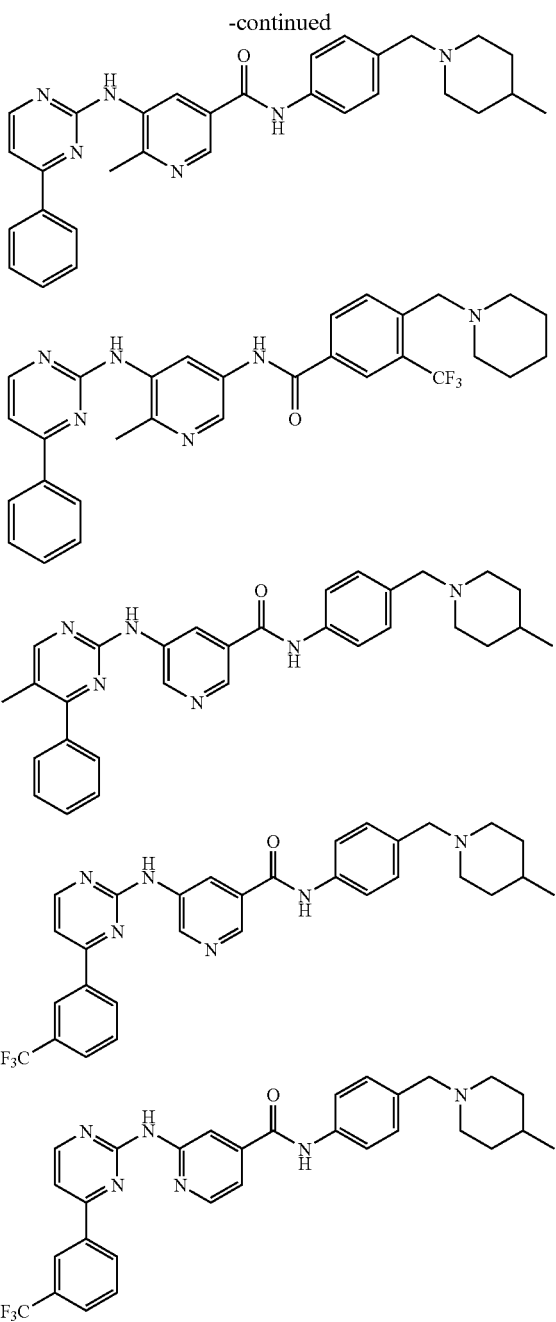

The invention therefore comprises any of the following:
1.1 Compounds of Formula (Q) or Formula (I), wherein W is —O— or —N(C$_{0-6}$alkyl)-;
1.2 Compounds of Formula (Q) or Formula (I) or 1.1, wherein W is —N(C$_{0-6}$alkyl)-;
1.3 Compounds of Formula (Q) or Formula (I) or 1.1 or 1.2, wherein W is —NH—;
1.4 Compounds of Formula (Q) or Formula (I), 1.1-1.3, wherein Y is —NHCO—, —CONH—, —NHSO$_2$—, —NHCONH—, or —NHCH$_2$—;
1.5 Compounds of Formula (Q) or Formula (I), or any of 1.1-1.4, wherein Y is —NHSO$_2$—;
1.6 Compounds of Formula (Q) or Formula (I), or any of 1.1-1.4, wherein Y is —CONH—;
1.7 Compounds of Formula (Q) or Formula (I), or any of 1.1-1.4, wherein Y is —NHCO—;
1.8 Compounds of Formula (Q) or Formula (I) or any of 1.1-1.7, wherein A$^1$ is —N—;
1.9 Compounds of Formula (Q) or Formula (I) or any of 1.1-1.7, wherein A$^1$ is —C(R$^7$)—;
1.10 Compounds of Formula (Q) or Formula (I) or any of 1.1-1.7 or 1.9, wherein A$^1$ is —C(H)—;
1.11 Compounds of Formula (Q) or Formula (I) or any of 1.1-1.10, wherein A$^2$ is —N—;
1.12 Compounds of Formula (Q) or Formula (I) or any of 1.1-1.10, wherein A$^2$ is —C— optionally is substituted with R$^8$;
1.13 Compounds of Formula (Q) or Formula (I) or any of 1.1-1.12, wherein A$^3$ is —N—;
1.14 Compounds of Formula (Q) or Formula (I) or any of 1.1-1.11, wherein A$^3$ is —C— optionally is substituted with R$^8$;
1.15 Formula 1.14, wherein R$^8$ is hydrogen, halo, C$_{1-4}$alkyl (e.g., methyl), C$_{1-4}$alkoxyl (e.g., methoxy), or haloC$_{1-4}$alkyl (e.g., trifluoromethyl);
1.16 Formula 1.14 or 1.15, wherein R$^8$ is hydrogen
1.17 Formula 1.14, wherein R$^8$ is C$_{1-4}$alkyl (e.g., methyl);
1.18 Compounds of Formula (Q) or Formula (I) or any of 1.1-1.17, wherein D is a 5 or 6 membered aryl, hetaryl or hetcyclic ring having at least one N, S, or O ring atom or a C ring atom forming an oxo (C=O) moiety;
1.19 Compounds of Formula (Q) or Formula (I) or any of 1.1-1.18, wherein D is a 5 or 6 membered aryl, hetaryl or hetcyclic ring having at least one N, S, or O ring atom;
1.20 Compounds of Formula (Q) or Formula (I) or any of 1.1-1.19, wherein D is aryl;
1.21 Compounds of Formula (Q) or Formula (I) or any of 1.1-1.20, wherein D is phenyl;
1.22 Compounds of Formula (Q) or Formula (I) or any of 1.1-1.21, wherein R$^1$ is C$_{1-6}$alkyl, aryl, or hetaryl; optionally substituted except at the ortho position of the aryl or hetaryl with 1-6 halo, C$_{1-6}$alkoxy, C$_{1-6}$alkyl, or trifluoromethyl substituents;
1.23 Compounds of Formula (Q) or Formula (I) or any of 1.1-1.22, wherein R$^1$ is aryl optionally substituted except at the ortho position of the aryl with 1-6 halo, C$_{1-6}$alkoxy, C$_{1-6}$alkyl, or trifluoromethyl substituents;
1.24 Compounds of Formula (Q) or Formula (I) or any of 1.1-1.23, wherein R$^1$ is phenyl optionally substituted except at the ortho position of the phenyl with 1-6 halo, C$_{1-6}$alkoxy, C$_{1-6}$alkyl, or trifluoromethyl;
1.25 Compounds of Formula (Q) or Formula (I) or any of 1.1-1.24, wherein R$^1$ is phenyl;
1.26 Compounds of Formula (Q) or Formula (I) or any of 1.1-1.25, wherein R$^1$ is p-methoxyphenyl, m-trifluoromethylphenyl or p-methylphenyl;
1.27 Compounds of Formula (Q) or Formula (I) or any of 1.1-1.22, wherein R$^1$ is hetaryl optionally substituted except at the ortho position of the hetaryl with 1-6 halo, C$_{1-6}$alkoxy, C$_{1-6}$alkyl, or trifluoromethyl substituents;
1.28 Compounds of Formula (Q) or Formula (I) or any of 1.1-1.22 or 1.27, wherein R$^1$ is pyridyl;
1.29 Compounds of Formula (Q) or Formula (I) or any of 1.1-1.22 or 1.27-1.28, wherein R$^1$ is pyrid-3-yl;
1.30 Compounds of Formula (Q) or Formula (I) or any of 1.1-1.29, wherein R$^2$ is C$_{0-6}$alkyl, C$_{3-7}$cycloalkyl, aryl, hetaryl, aryl(C$_{1-4}$alkyl)-, hetcyclyl(C$_{0-4}$alkyl)-, or —C$_{0-6}$alkyl-N(C$_{0-6}$alkyl)(C$_{0-6}$alkyl), optionally substituted with C$_{1-6}$alkyl;
1.31 Compounds of Formula (Q) or Formula (I) or any of 1.1-1.30, wherein R$^2$ is hetcyclyl(C$_{0-4}$alkyl)- optionally substituted with C$_{1-6}$alkyl;
1.32 Compounds of Formula (Q) or Formula (I) or any of 1.1-1.31, wherein R$^2$ is piperidin-1-yl(C$_{0-4}$alkyl)-, piperidin-4-yl($C_{0-4}$alkyl)-, piperazin-1-yl($C_{0-4}$alkyl) or piperazin-4-yl($C_{0-4}$alkyl), optionally substituted with $C_{1-6}$alkyl;

1.33 Compounds of Formula (Q) or Formula (I) or any of 1.1-1.32, wherein $R^2$ is piperidin-1-ylmethyl-, 4-methylpiperidin-1-ylmethyl, N-methylpiperidin-4-ylmethyl-, piperazin-1-ylmethyl, 4-methylpiperazin-1-ylmethyl or 4-ethylpiperazin-1-ylmethyl;

1.34 Compounds of Formula (Q) or Formula (I) or any of 1.1-1.33, wherein $R^3$, $R^4$, $R^5$, $R^6$, $R^7$ and $R^8$ are independently selected from hydrogen, halo, $C_{1-4}$alkyl (e.g., methyl), $C_{1-4}$alkoxyl (e.g., methoxy), and halo$C_{1-4}$alkyl (e.g., trifluoromethyl);

1.35 Compounds of Formula (Q) or Formula (I) or any of 1.1-1.34, wherein $R^3$ is hydrogen;

1.36 Compounds of Formula (Q) or Formula (I) or any of 1.1-1.35, wherein $R^4$ is hydrogen;

1.37 Compounds of Formula (Q) or Formula (I) or any of 1.1-1.36, wherein $R^4$ is $C_{1-4}$alkyl (e.g., methyl);

1.38 Compounds of Formula (Q) or Formula (I) or any of 1.1-1.35 or 1.37, wherein $R^4$ is methyl;

1.39 Compounds of Formula (Q) or Formula (I) or any of 1.1-1.38, wherein, the present invention comprises any of the following compounds:

in free or salt form.

The term "alkyl" includes both straight and branched chain alkyl groups. References to individual alkyl groups such as "propyl" are specific for the straight chain version only and references to individual branched chain alkyl groups such as 'isopropyl' are specific for the branched chain version only. For example, "$C_{1-6}$alkyl" includes $C_{1-4}$alkyl, $C_{1-3}$alkyl, propyl, isopropyl and t-butyl. A similar convention applies to other radicals, for example "phenyl$C_{1-6}$alkyl" includes phenyl$C_{1-4}$alkyl, benzyl, 1-phenylethyl and 2-phenylethyl. "$C_0$alkyl" refers to a hydrogen terminus when the $C_0$alkyl is terminal and refers to a direct bond when the "$C_0$alkyl" is bridging (linking). The term "$C_{0-6}$alkyl", for example, refers to adding "$C_0$alkyl" to the scope of the "$C_{1-6}$alkyl" definition. Thus, it is understood that substituents allowed for "$C_{1-6}$alkyl" would accordingly be allowed for the "$C_{1-6}$alkyl" within the scope of "$C_{0-6}$alkyl".

The term "halo" refers to fluoro, chloro, bromo and iodo.

Where optional substituents are chosen from, for example, "1-5 independent" substituents from a list of substituents, it is to be understood that this definition includes all substituents being chosen from one of the specified groups or the substituents being chosen from two or more of the specified groups in the list. Where a substituent is recited using the molecule (parent) name, it is understood that the substituent is the radical of such molecular parent.

An "aryl" is well understood by one in the art and includes phenyl and naphthyl.

A "hetaryl" is a 4-12 membered fully unsaturated or partially unsaturated heterocyclic mono or bicyclic ring containing at least one nitrogen, sulphur or oxygen ring atom and in which, unless otherwise specified, a —$CH_2$— group can optionally be replaced by a —C(O)—. Examples of such hetaryl include indolyl, pyridyl, furyl, thienyl, pyranyl, pyrrolyl, pyrazolyl, isothiazolyl, isobenzofuranyl, 2,3-dihydrobenzofuranyl, imidazo[1,2-a]pyridinyl, benzimidazolyl quinolyl, pyrrolinyl, imidazolyl, pyrimidyl, pyrazinyl, pyridazinyl, isoxazolyl, benzoxazolyl, benzoxazol-2-one, benzopyridazin-dione, pyridine-N-oxide, and quinoline-N-oxide.

A "hetcyclyl" is a saturated, mono or bicyclic ring containing 4-12 atoms containing at least one nitrogen, sulphur or oxygen ring atom. Examples of such "hetcyclyl" include pyrrolidinyl, imidazolidinyl, pyrazolininyl, tetrahydropyranyl, morpholino, piperidyl, and piperazinyl.

Examples of "$C_{1-6}$alkoxy" include methoxy, ethoxy and propoxy.

Examples of "—($C_{0-6}$alkyl)-N($C_{0-6}$alkyl)($C_{0-6}$alkyl)" include methylamino, ethylamino, di-N-methylamino, di-(N-ethyl)amino, and N-ethyl-N-methylamino.

A suitable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine. The Compounds of the Invention, e.g., compounds of formula (Q) or formula (I), e.g., any of 1.1-1.39, are intended for use as pharmaceuticals, therefore pharmaceutically acceptable salts are preferred. Salts which are unsuitable for pharmaceutical uses may nevertheless be useful, for example, for the isolation or purification of free Compounds of the Invention. Consequently, the present invention encompasses novel Compounds of Formula (Q) and formula (I), in free or salt form, including salts that are suitable as well as salts which are unsuitable for pharmaceutical use.

According to a further aspect of the invention there is provided a pharmaceutical composition which comprises a compound of the formula (I), or a pharmaceutically acceptable salt thereof, as defined hereinbefore, in association with a pharmaceutically-acceptable diluent or carrier. In another aspect of the invention, there is provided a pharmaceutical composition which comprises a compound of formula (Q) or formula (I), e.g., any of 1.1-1.39, in free or pharmaceutically acceptable salt form, in association with a pharmaceutically acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 1-1000 mg/kg, and this normally provides a therapeutically-effective dose. Preferably a daily dose in the range of 10-100 mg/kg is employed. Similarly, the compound of formula (Q) or any of 1.1-1.39 may also be administered to a warm-blooded animal at a unit dose within the range of 1-1000 mg/kg, preferably a daily dose in the range of 10-100 mg/kg. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt thereof, as defined hereinbefore for use in a method of treatment of the human or animal body by therapy. The invention also provides a compound of formula (Q), or any of 1.1-1.39, in free or pharmaceutically acceptable salt form, for use in a method of treatment of the human or animal body by therapy.

We have found that the compounds defined in the present invention, or a pharmaceutically acceptable salt thereof, can penetrate the blood-brain barrier and inhibit the formation and accumulation of beta-amyloid. Accordingly the compounds of the present invention are useful in the treatment of neurodegenerative diseases, particularly Alzheimer's disease. Therefore, the invention provides a compound of formula (Q) or formula (I), e.g., any of 1.1-1.39, in free or pharmaceutically acceptable salt form, which penetrates the blood-brain barrier and inhibit the formation and accumulation of beta-amyloid. The invention also provides a compound of formula (Q) or formula (I), e.g., any of 1.1-1.39, in free or pharmaceutically acceptable salt form, useful for the treatment of neurodegenerative diseases, particularly Alzheimer's disease.

We have found that the compounds defined in the present invention, or a pharmaceutically acceptable salt thereof, can inhibit certain kinases. Accordingly the compounds of the present invention are useful in the treatment of cancers of the central nervous system. Therefore, the invention provides a compound of formula (q) or formula (I), e.g., any of 1.1-1.39, in free or pharmaceutically acceptable salt form, useful in the treatment of cancers of the central nervous system.

Thus according to this aspect of the invention there is provided a compound of the formula (I), or a pharmaceutically acceptable salt thereof, as defined hereinbefore for use as a medicament.

According to a further aspect of the invention there is provided the use of a compound of the formula (I), or a pharmaceutically acceptable salt thereof, as defined hereinbefore in the manufacture of a medicament for use in the inhibition of the formation and accumulation of beta-amyloid in a warm-blooded animal such as man. Use of a compound of the formula (Q) or formula (I), e.g., any of 1.1-1.39, in free or pharmaceutically acceptable salt form, as defined hereinbefore in the manufacture of a medicament for use in the inhibition of the formation and accumulation of beta-amyloid in a warm-blooded animal such as man.

According to an aspect of the invention there is provided the use of a compound of the formula (I), or a pharmaceutically acceptable salt thereof, as defined hereinbefore in the manufacture of a medicament for use in the production of an inhibition of certain kinases across the blood-brain barrier in a warm-blooded animal such as man. In another aspect, the invention also provides use of a compound for formula (Q) or formula (I), e.g., any of 1.1-1.39, in free or pharmaceutically acceptable salt form, in the manufacture of a medicament for use in the production of an inhibition of certain kinases across the blood-brain barrier in a warm-blooded animal such as a man.

According to a further feature of the invention, there is provided the use of a compound of the formula (I), in free or salt form, as defined herein before in the manufacture of a medicament for use in the treatment of cancers of the nervous system and the brain. In still another feature of the invention, there is provided use of a compound of the formula (Q) or formula (I), e.g., any of 1.1-1.39, in free or pharmaceutically acceptable salt form, as defined herein before in the manufacture of a medicament for use in the treatment of cancers of the nervous system and the brain.

According to a further feature of this aspect of the invention there is provided a method for producing an inhibitory effect against the accumulation of abnormal protein aggregates in a warm-blooded animal, such as man, in need of such treatment which comprises administering to said animal an effective amount of a compound of formula (I), or a pharmaceutically acceptable salt thereof. In still another feature of this aspect of the invention, there is provided a method for producing an inhibitory effect against the accumulation of abnormal protein aggregates in a warm-blooded animal, such as man, in need of such treatment which comprises administering to said animal an effective amount of a compound of formula (Q) or formula (I), e.g., any of 1.1-1.39, in free or pharmaceutically acceptable salt form.

Furthermore, the compounds of this invention are useful in the treatment, control and management of diseases characterized by accumulation of abnormal protein aggregates, especially in the brain—for example, diseases such as Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloidosis, Parkinson's disease, Huntington's disease, prion disease and/or vascular, neurological, and/or neurodegenerative disorders related to the abnormal expression or accumulation of tau or amyloid proteins such as Aβ. Such abnormal protein aggregates include, for example, i) amyloid plaques and neurofibrillary tangles, and ii) precipitates of tau or amyloid proteins such as Aβ.

Accordingly, the present invention provides methods of treatment of Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloeiosis, Parkinson's disease, Huntington's disease, prion disease and/or vascular, neurological, and/or neurodegenerative disorders related to the abnormal expression or accumulation of tau or amyloid proteins such as Aβ. Therefore, the invention provides a method for the treatment of Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloeiosis, Parkinson's disease, Huntington's disease, prion disease and/or vascular, neurological, and/or neurodegenerative disorders related to the abnormal expression or accumulation of tau or amyloid proteins such as Aβ, which method comprises administering to a patient in need thereof, a compound of formula (Q) or formula (I), e.g., any of 1.1-1.39, in free or pharmaceutically acceptable salt form.

Additionally, the present invention provides methods of treatment of hyperproliferative diseases, especially cancers of the brain or central nervous system, including astrocytoma, medulloblastoma, oligdendroglioma, glioblastoma, glioma, ependymoma, meningioma, sarcoma, germ cell tumor, pinealoma, craniopharyngioma, and pituitary adenoma. The present invention also provides methods of treatment of hyperproliferative diseases as described herein comprising administering to a patient in need thereof a compound of formula (Q) or formula (I), e.g., any of 1.1-1.39, in free or pharmaceutically acceptable salt form.

The present invention also provides methods of treatment of disease characterized by dysfunctional expression or activity of kinases such as the c-Abl, BCR-Abl, ARG, c-Src, c-Kit, FAK, Trk, EGFR, VEGFR, Tie-2, c-Met, FGFR-1, Flt-1, Her-2, c-Raf, PDGFR, PDGFR-beta, MAPK, PKA, PKC, PKCα, PKCδ, CDK5, GSK-3, or JNK, especially over-expression or over-activity of kinases in CNS cells, comprising the administration of an effective amount of a compound or composition of the present invention in free or salt form to a human or animal patient in need thereof. The compound or composition of the present invention includes compounds of formula (Q) or formula (I), e.g., any of 1.1-1.39, in free or pharmaceutically acceptable salt form.

In a further aspect of the invention there is provided a pharmaceutical composition which comprises a compound of the formula (I), or a pharmaceutically acceptable salt thereof, as defined herein before in association with a pharmaceutically-acceptable diluent or carrier for use in the treatment, control and management of diseases characterized by accumulation of abnormal protein aggregates, especially in the brain, such as Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloidosis, Parkinson's disease, Huntington's disease, prion disease and/or vascular, neurological, and/or neurodegenerative disorders related to the abnormal expression or accumulation of tau or amyloid proteins such as Aβ. In another embodiment, the invention provides a pharmaceutical composition which comprises a compound of the formula (Q) or formula (I), e.g., any of 1.1-1.39, in free or pharmaceutically acceptable salt form, as defined herein before in association with a pharmaceutically-acceptable diluent or carrier for use in the treatment, control and management of diseases characterized by accumulation of abnormal protein aggregates, especially in the brain, such as Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloidosis, Parkinson's disease, Huntington's disease, prion disease and/or vascular, neurological, and/or neurodegenerative disorders related to the abnormal expression or accumulation of tau or amyloid proteins such as Aβ. Such abnormal protein aggregates include, for example, i) amyloid plaques and neurofibrillary tangles, and ii) precipitates of tau or amyloid proteins such as Aβ.

In a further aspect of the invention there is provided a pharmaceutical composition which comprises a compound of the formula (I), or a pharmaceutically acceptable salt thereof, as defined herein before in association with a pharmaceutically-acceptable diluent or carrier for use in the treatment of Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloeiosis, Parkinson's disease, Huntington's disease, prion disease and/or vascular, neurological, and/or neurodegenerative disorders related to the abnormal expression or accumulation of tau or amyloid proteins such as Aβ. In still another aspect of the invention, there is provided a pharmaceutical composition which comprises a compound of the formula (Q) or formula (I), any of 1.1-1.39, in free or pharmaceutically acceptable salt form, as defined herein before in association with a pharmaceutically acceptable diluent or carrier for use in the treatment of Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloeiosis, Parkinson's disease, Huntington's disease, prion disease and/or vascular, neurological, and/or neurodegenerative disorders related to the abnormal expression or accumulation of tau or amyloid proteins such as Aβ.

The treatment methods include administering the compounds of the present invention, e.g., a compound of formula (Q) or formula (I), e.g., any of 1.1-1.39, in free or salt form, together with other therapeutic compounds to treat Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloeiosis, Parkinson's disease, Huntington's disease, prion disease and/or vascular, neurological, and/or neurodegenerative disorders related to the abnormal expression or accumulation of tau or amyloid proteins such as Aβ.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of accumulation of abnormal protein aggregates, especially in the brain, as part of the search for new therapeutic agents.

In a further aspect of the invention there is provided a pharmaceutical composition which comprises a compound of the formula (I), or a pharmaceutically acceptable salt thereof, as defined herein before in association with a pharmaceutically-acceptable diluent or carrier for use in the of treatment of hyperproliferative diseases, especially cancers of the brain or central nervous system, including astrocytoma, medulloblastoma, oligdendroglioma, glioblastoma, glioma, ependymoma, meningioma, sarcoma, germ cell tumor, pinealoma, craniopharyngioma, and pituitary adenoma. In another aspect, the invention also provides a pharmaceutical composition which comprises a compound of formula (Q) or (I), e.g., any of 1.1-1.39, in free or pharmaceutically acceptable salt thereof, as defined herein before in association with a pharmaceutically-acceptable diluent or carrier for use in the of treatment of hyperproliferative diseases, especially cancers of the brain or central nervous system, including astrocytoma, medulloblastoma, oligdendroglioma, glioblastoma, glioma, ependymoma, meningioma, sarcoma, germ cell tumor, pinealoma, craniopharyngioma, and pituitary adenoma.

In a further aspect of the invention there is provided a pharmaceutical composition which comprises a compound of the formula (I), or a pharmaceutically acceptable salt thereof, as defined herein before in association with a pharmaceutically-acceptable diluent or carrier for use in the treatment of astrocytoma, medulloblastoma, oligdendroglioma, glioblastoma, glioma, ependymoma, meningioma, sarcoma, germ cell tumor, pinealoma, craniopharyngioma, and pituitary adenoma. In still another aspect, the invention provides a compound of the formula (Q) or formula (I), e.g., any of 1.1-1.39, in free or pharmaceutically acceptable salt form, as defined herein before in association with a pharmaceutically-acceptable diluent or carrier for use in the treatment of astrocytoma, medulloblastoma, oligdendroglioma, glioblastoma, glioma, ependymoma, meningioma, sarcoma, germ cell tumor, pinealoma, craniopharyngioma, and pituitary adenoma.

The treatment methods include administering the compounds of the present invention, e.g., compound of formula (Q) or formula (I), e.g., any of 1.1-1.39, in free or salt form, together with other therapeutic compounds to treat hyperproliferative diseases, especially cancers of the brain or central nervous system, including astrocytoma, medulloblastoma, oligdendroglioma, glioblastoma, glioma, ependymoma, meningioma, sarcoma, germ cell tumor, pinealoma, craniopharyngioma, and pituitary adenoma.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

In addition to their use in therapeutic medicine, the compounds of formula (I) and their pharmaceutically acceptable salts are also useful as pharmacological tools in the development and standardisation of in vitro and in vivo test systems for the evaluation of the effects of dysfunctional expression or activity of kinases such as the c-Abl, BCR-Abl, ARG, c-Src, c-Kit, FAK, Trk, EGFR, VEGFR, Tie-2, c-Met, FGFR-1, Flt-1, Her-2, c-Raf, PDGFR, PDGFR-beta, MAPK, PKA, PKC, PKCα, PKCδ, CDK5, GSK-3, or JNK, especially overexpression or over-activity of kinases in CNS cells, as part of the search for new therapeutic agents. Similarly, the compounds of formula (Q), e.g., any of 1.1-1.39, in free or pharmaceutically acceptable salt forms, are also useful as pharmacological tools in the development and standardisation of in vitro and in vivo test systems for the evaluation of the effects of dysfunctional expression or activity of kinases as hereinbefore described.

In the above other pharmaceutical composition, process, method, use and medicament manufacture features, the alternative and preferred embodiments of the compounds of the invention described herein also apply.

EXAMPLES

The invention will now be illustrated by the following non limiting examples in which, unless stated otherwise:
(i) temperatures are given in degrees Celsius (° C.); operations were carried out at room or ambient temperature ("rt") were at a temperature in the range of 18-25° C.;
(ii) organic solutions were dried over anhydrous sodium sulphate; evaporation of solvent is carried out using a rotary evaporator under reduced pressure (600-4000 Pascals; 4.5-30 mmHg) with a bath temperature of up to 60° C.;
(iii) in general, the course of reactions is followed by TLC and reaction times are given for illustration only;
(iv) final products had satisfactory proton nuclear magnetic resonance (NMR) spectra and/or mass spectral data;
(v) yields are given for illustration only and are not necessarily those which can be obtained by diligent process development; preparations were repeated if more material is required;
(vii) when given, NMR data is in the form of delta values for major diagnostic protons, given in parts per million (ppm) relative to tetramethylsilane (TMS) as an internal standard, determined at 400 MHz using perdeuterio dimethyl sulphoxide (DMSO-$d_6$) as solvent unless otherwise indicated;
(vii) chemical symbols have their usual meanings; SI units and symbols are used;
(viii) solvent ratios are given in volume:volume (v/v) terms; and
(ix) mass spectra were run with an electron energy of 70 electron volts in the chemical ionization (CI) mode using a direct exposure probe; where indicated ionization is effected by electron impact (EI), fast atom bombardment (FAB) or electrospray (ESP); values for m/z are given; generally, only ions which indicate the parent mass are reported; and unless otherwise stated, the mass ion quoted is [MH]+;

(x) where a synthesis is described as being analogous to that described in a previous example the amounts used are the millimolar ratio equivalents to those used in the previous example;

(xi) the following abbreviations have been used:

| | |
|---|---|
| $Cs_2CO_3$ | cesium carbonate; |
| HOBt | 1H-benzo[d][1,2,3]triazol-1-ol; |
| HPLC | high performance liquid chromatography; |
| MeOH | methanol; |
| $NaHCO_3$ | sodium bicarbonate; |
| BOP | benzotriazol-1-yloxytris(dimethylamino)phosphonium hexafluorophosphate; |
| THF | tetrahydrofuran; |
| DMF | N,N-dimethylformamide; |
| EtOAc | ethyl acetate; |
| DIEA | N,N-diisopropylethylamine; |
| DCM | dichloromethane; |
| DMSO | dimethylsulphoxide; and |
| MeCN | acetonitrile; |

(xii) "ISCO" refers to normal phase flash column chromatography using 12 g and 40 g pre-packed silica gel cartridges used according to the manufacturer's instructions obtained from ISCO, Inc, 4700 superior street Lincoln, Nebr., U.S.A.

Example 1

4-((4-ethylpiperazin-1-yl)methyl)-N-(6-methyl-5-(4-(pyridin-3-yl)pyrimidin-2-ylamino)pyridin-3-yl)benzamide

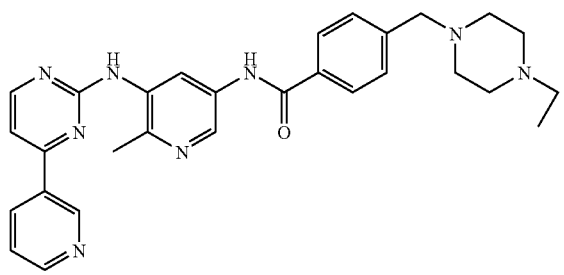

(a) (2-Methyl-5-nitro-pyridin-3-yl)-(4-pyridin-3-yl-pyrimidin-2-yl)-amine

To a mixture of 3-bromo-2-methyl-5-nitro-pyridine (380 mg, 1.75 mmol) and 4-pyridin-3-yl-pyrimidin-2-ylamine (250 mg, 1.45 mmol) in dry toluene (20 mL) were added $Cs_2CO_3$ (710 mg, 2.18 mmol), $Pd_2(dba)_3$ (26 mg, 0.028 mmol) and Xantphos (50 mg, 0.086 mmol). The mixture was evacuated and purged with $N_2$ (3 cycles), heated to 90° C. under $N_2$ for 16 h. After completion (monitored by TLC), the reaction mixture was cooled to rt, diluted with EtOAc and filtered. The filtrate was concentrated under reduced pressure and the residue was purified by column chromatography ($SiO_2$) using $CH_2Cl_2$-MeOH (98:2) to afford product (225 mg, 50%). $^1$H NMR (200 MHz, $CDCl_3$): δ 2.76 (s, 3H), 7.23 (m, 1H), 7.38 (d, J=6.0 Hz, 1H), 7.51 (m, 1H), 8.51 (m, 1H), 8.63 (d, J=6.0 Hz, 1H), 8.77 (m, 1H), 9.04 (d, J=2.0 Hz, 1H), 9.28 (d, J=2.0 Hz, 1H), 9.77 (d, J=2.0 Hz, 1H); Mass [M+H]+: 309.

(b) 2-Methyl-$N^3$-(4-pyridin-3-yl-pyrimidin-2-yl)-pyridine-3,5-diamine

A mixture of (2-methyl-5-nitro-pyridin-3-yl)-(4-pyridin-3-yl-pyrimidin-2-yl)-amine (450 mg, 11.84 mmol), catalytic ferric chloride (50 mg) in hydrazine hydrate (20 mL) and methanol (20 mL) was refluxed for 1 h. The reaction mixture was cooled to rt, concentrated under reduced pressure and the crude residue was diluted with water (10 mL) and extracted with EtOAc (2×25 mL). The combined extracts were dried over anhydrous $Na_2SO_4$, filtered, concentrated under reduced pressure. The residue was stirred with hexane (20 mL) for 5 min, the hexane layer was decanted and the residue was dried to give 280 mg of product as a pale yellow solid (Yield: 68%). Mp: 135° C.; $^1$H NMR (200 MHz, $CDCl_3$): δ 2.51 (s, 3H), 3.65 (bs, 2H), 6.99 (s, 1H), 7.22 (d, J=4.0 Hz, 1H), 7.44 (m, 1H), 7.78 (d, J=10.0 Hz, 1H), 8.05 (d, J=2 Hz, 1H), 8.36-8.31 (m, 1H), 8.51 (d, J=4.0 Hz, 1H), 8.75-8.72 (m, 1H), 9.27 (d, J=2.0 Hz, 1H); Mass [M+H]+: 279.

(c) 4-((4-ethylpiperazin-1-yl)methyl)-N-(6-methyl-5-(4-(pyridin-3-yl)pyrimidin-2-ylamino)pyridin-3-yl)benzamide DIEA (47 μL, 0.27 mmol) was added into a solution of 2-Methyl-$N^3$-(4-pyridin-3-yl-pyrimidin-2-yl)-pyridine-3,5-diamine (15 mg, 0.054 mmol), 4-((4-ethylpiperazin-1-yl)methyl)benzoic acid (16.1 mg, 0.61 mmol), BOP (33.4 mg, 0.76 mmol) in DMF (1.5 mL). The reaction mixture is stirred at rt under argon atmosphere overnight. The reaction mixture was then purified by Waters semi-preparative HPLC to the final product. MS (ESI+) m/z 509.1 [M+H]+.

Example 2

4-((4-ethylpiperazin-1-yl)methyl)-N-(6-methyl-5-(4-phenylpyrimidin-2-ylamino)pyridin-3-yl)benzamide

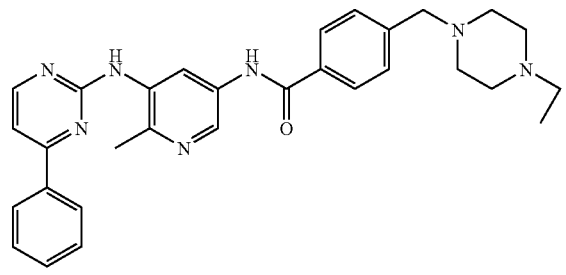 [SMILES: CCN1CCN(Cc2ccc(C(=O)Nc3cnc(C)c(Nc4nccc(-c5ccccc5)n4)c3)cc2)CC1]

The synthesis method is analogous to EXAMPLE 1 wherein 4-phenylpyrimidin-2-amine was added in step (a) instead of 4-pyridin-3-yl-pyrimidin-2-ylamine (overall yield: 33.7%). MS (ESI+) m/z 508.1 [M+H]+.

Example 3

N-(6-methyl-5-(4-phenylpyrimidin-2-ylamino)pyridin-3-yl)-4-((1-methylpiperidin-4-yl)methyl)benzamide

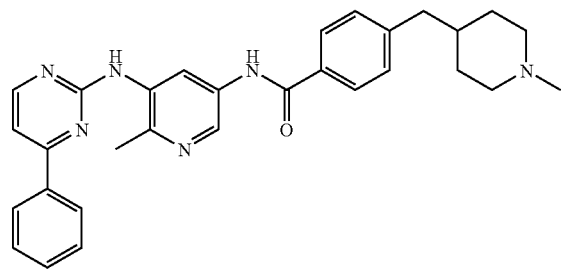

The synthesis method is analogous to EXAMPLE 1 wherein 4-phenylpyrimidin-2-amine was added in step (a)

instead of 4-pyridin-3-yl-pyrimidin-2-ylamine, and 4-((1-methylpiperidin-4-yl)methyl)benzoic acid was used in step (c) instead of 4-((4-ethylpiperazin-1-yl)methyl)benzoic acid (overall yield: 10.2%). MS (ESI⁺) m/z 493.1 [M+H]⁺.

Example 4

N-(6-methyl-5-(4-(pyridin-3-yl)pyrimidin-2-ylamino)pyridin-3-yl)picolinamide

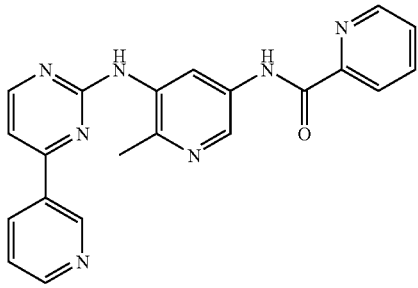

Picolinoyl chloride hydrochloride salt (96 mg, 0.54 mmol) was added into a solution of 2-methyl-N³-(4-pyridin-3-yl-pyrimidin-2-yl)-pyridine-3,5-diamine (50 mg, 0.18 mmol) in pyridine (1.5 mL). The reaction mixture was stirred at rt under argon atmosphere overnight. After pyridine is removed under reduced pressure, the residue is purified by chromatography to give 10.4 mg of the product as pale yellow solids (Yield: 15%). MS (ESI⁺) m/z 384.3 [M+H]⁺

Example 5

N-(6-methyl-5-(4-phenylpyrimidin-2-ylamino)pyridin-3-yl)picolinamide

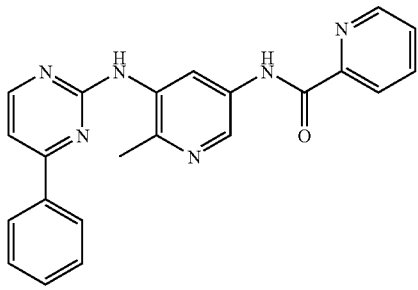 [SMILES: Cc1ncc(NC(=O)c2ccccn2)cc1Nc1nccc(-c2ccccc2)n1]

Picolinoyl chloride hydrochloride salt (64 mg, 0.36 mmol) was added into a solution of 2-methyl-N-3-(4-phenylpyrimidin-2-yl)pyridine-3,5-diamine (50 mg, 0.18 mmol) in pyridine (2.5 mL). The reaction mixture was stirred at rt under argon atmosphere for about 60 h. After pyridine is removed under reduced pressure, the residue is purified by chromatography to give 9.1 mg of the product as pale yellow solids (Yield: 13%). MS (ESI⁺) m/z 383.2 [M+H]⁺

Example 6

N-(4-((4-methylpiperidin-1-yl)methyl)phenyl)-5-(4-phenylpyrimidin-2-ylamino)nicotinamide

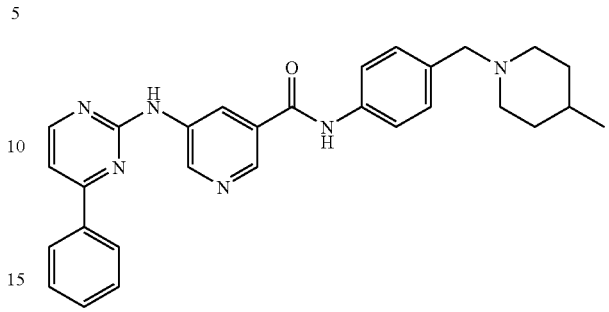

(a) 5-bromo-N-(4-((4-methylpiperidin-1-yl)methyl)phenyl)nicotinamide

DIEA (473 μL, 2.72 mmol) was added into a solution of 5-bromonicotinic acid (178 mg, 0.881 mmol), 4-((4-methylpiperidin-1-yl)methyl)benzenamine (150 mg, 0.734 mmol), BOP (487 mg, 1.10 mmol) in DMF (3 mL). The reaction mixture is stirred at rt under argon atmosphere overnight. The reaction mixture was diluted with 80 mL of AcOEt, and then washed with 1N NaOH aqueous solution three times. Organic phase was dried with anhydrous Na₂SO₄, and then evaporated to remove organic solvents. The obtained residue was further dried under high vacuum overnight to give crude product, which was used directly for the next step synthesis without further purification. MS (ESI⁺) m/z 388.1 [M+H]⁺.

(b) N-(4-((4-methylpiperidin-1-yl)methyl)phenyl)-5-(4-phenylpyrimidin-2-ylamino)nicotinamide A mixture of 5-bromo-N-(4-((4-methylpiperidin-1-yl)methyl)phenyl)nicotinamide (45.6 mg, 0.1 mmol) and 4-phenylpyrimidin-2-amine (25.7 mg, 0.15 mmol), KOBuᵗ (22.4 mg, 0.2 mmol), Pd₂(dba)₃ (4.6 mg, 0.005 mmol) and Xantphos (4.6 mg, 0.008 mmol) in a microwave reaction vessel was suspended in 2 mL of THF. The reaction mixture was heated in a microwave at 150° C. for 90 min. After cooling, the mixture was diluted with DMF, and then filtered with a 0.45 μm microfilter. The obtained filtrate was separated by a semi-preparative HPLC. Collected product fraction was lyophilized to give pure product as a while powder (20 mg, 38%). MS (ESI⁺) m/z 479.2 [M+H]⁺.

Example 7

N-(6-methyl-5-(4-phenylpyrimidin-2-ylamino)pyridin-3-yl)-4-((1-methylpiperidin-4-yl)methyl)benzamide

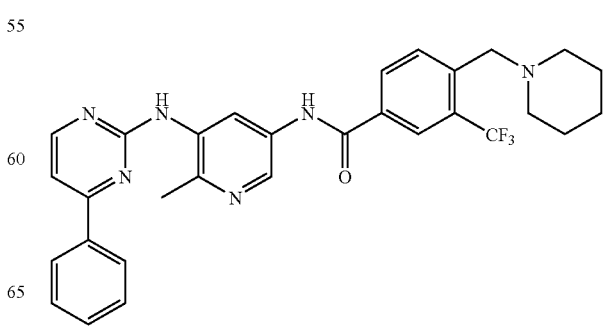

The synthesis method is analogous to EXAMPLE 1 wherein 4-phenylpyrimidin-2-amine was added in step (a) instead of 4-pyridin-3-yl-pyrimidin-2-ylamine, and 4-(piperidin-1-ylmethyl)-3-(trifluoromethyl)benzoic acid was used in step (c) instead of 4-((4-ethylpiperazin-1-yl)methyl)benzoic acid. MS (ESI+) m/z 547.1 [M+H]+.

Example 8

5-(5-methyl-4-phenylpyrimidin-2-ylamino)-N-(4-((4-methylpiperidin-1-yl)methyl)phenyl)nicotinamide

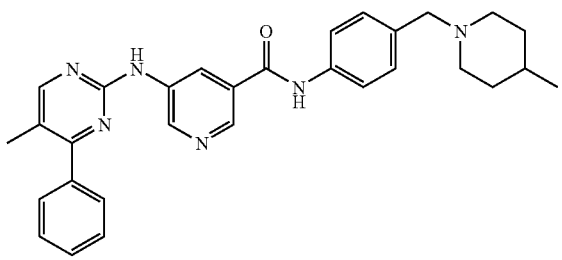

The synthesis method is analogous to EXAMPLE 6 wherein 5-methyl-4-phenylpyrimidin-2-amine was added in step (b) instead of 4-phenylpyrimidin-2-amine. MS (ESI+) m/z 493.2 [M+H]+.

Example 9

N-(4-((4-methylpiperidin-1-yl)methyl)phenyl)-5-(4-(3-(trifluoromethyl)phenyl)pyrimidin-2-ylamino) nicotinamide

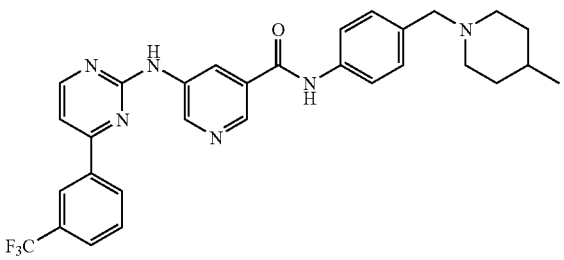

The synthesis method is analogous to EXAMPLE 6 wherein 4-(3-(trifluoromethyl)phenyl)pyrimidin-2-amine was added in step (b) instead of 4-phenylpyrimidin-2-amine. MS (ESI+) m/z 547.2 [M+H]+.

Example 10

N-(4-((4-Methylpiperidin-1-yl)methyl)phenyl)-2-(4-(3-(trifluoromethyl)phenyl)pyrimidin-2-ylamino) isonicotinamide

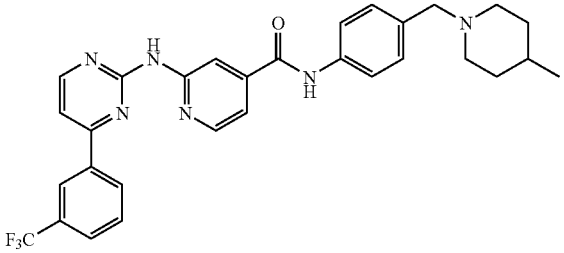

The synthesis method is analogous to EXAMPLE 6 wherein 2-bromoisonicotinic acid was added in step (a) instead of 5-bromonicotinic acid, and 4-(3-(trifluoromethyl)phenyl)pyrimidin-2-amine was added in step (b) instead of 4-phenylpyrimidin-2-amine. MS (ESI+) m/z 547.2 [M+H]+.

Example 11

N2a Cell Assay

Evaluation of Amyloid Beta (Aβ) Production in N2a Cells.

The influence of compounds on Aβ production in N2a cells is carried out as described by Netzer, W. J., Dou, F., Cai, D., Veach, D., Jean, S., Li, Y., Bornmann, W. G., Clarkson, B., Xu, H., and Greengard, P. (2003) *Proc Natl Acad Sci USA* 100, 12444-12449. The exemplified Compounds of the Invention inhibit amyloid beta by at least 50% at concentrations 10 micromolar over 24 hours.

Example 12

Mouse Brain/Plasma Distribution Assay for the Evaluation of Tissue Levels of Test Compounds Compounds are administered sub-cutaneously to C57bl/6 black mice as a single injection of 1 mg using a 10 mM DMSO solution. After 2 or 4 hours, the mice are sacrificed. Trunk blood is collected into tubes with potassium-EDTA as anticoagulant and centrifuged at 5000×g for 10 min. The upper plasma phase is decanted from cellular components. Whole brain is sonicated with 20 mM Tris-HCl, 135 mM NaCl, pH 7.4 buffer, giving at 200 mg/mL (w/v) homogenate. Brain homogenate or plasma is extracted with 2 volumes of acetonitrile and clarified by centrifugation at 15,000×g for 20 min. Extracts are separated by HPLC using a Waters Alliance 2695 separations module with a Sunfire™ C18 column (3.5 micron, 2.1×50 mm) and a gradient of methanol over 15 min in a mobile phase of 0.1% formic acid. The separation is monitored by a Micromass Quattro Micro triple-quadrupole mass-spectrometric detector. Compound standardization is performed by methods analogous to those previously reported, e.g., by Zhao, M., et al. (2005) *J Chromatogr B Analyt Technol Biomed Life Sci* 819, 73-80; and Appels, N. M et al. (2005) *Rapid Commun Mass Spectrom* 19, 2187-2192.

Brain concentration=measured−2% of plasma

*B/P* ratio=brain concentration/plasma concentration

Exemplified Compounds of the Invention have a B/P ratio in this assay at four hours post-administration of greater than 0.6, while having a brain concentration of greater than 0.3 μM at four hours post administration compared to the brain concentration of imatinib at four hours post-administration of less than 0.1 μM, demonstrating a substantially higher level of penetration and accumulation in the brain for the Compounds of the Invention.

What is claimed:

1. A compound of formula (Q):

Formula (Q)

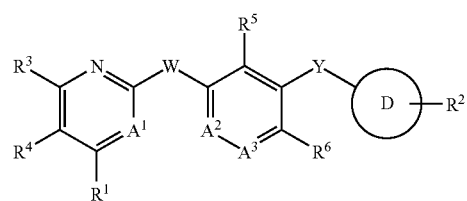

in free or salt form, wherein:
$A^1$ is —C($R^7$)— or —N—;
$A^2$ and $A^3$ are independently —C— or —N—, wherein at least one of $A^2$ and $A^3$ must be N; and wherein when $A^2$ or $A^3$ is —C—, it is optionally substituted with $R^8$;

W is —O— or —N(C$_{0-6}$alkyl)-;
Y is —NHCO—, —CONH—;
D is a 5 or 6 membered aryl, hetaryl or hetcyclic ring having at least one N, S, or O ring atom, or a C ring atom forming an oxo (C=O) moiety;
R$^1$ is phenyl; optionally substituted except at the ortho position of the phenyl with 1-6 halo, C$_{1-6}$alkoxy, C$_{1-6}$alkyl, or trifluoromethyl substituents; wherein the ortho phenyl position is unsubstituted;
R$^2$ is hetcyclyl(C$_{0-4}$alkyl)-, optionally substituted with C$_{1-6}$alkyl; and
R$^3$, R$^4$, R$^5$, R$^6$, R$^7$ and R$^8$ are independently selected from hydrogen, halo, C$_{1-4}$alkyl, C$_{1-4}$alkoxyl, and haloC$_{1-4}$alkyl.

2. The compound according to claim 1 wherein the compound of formula (Q) is

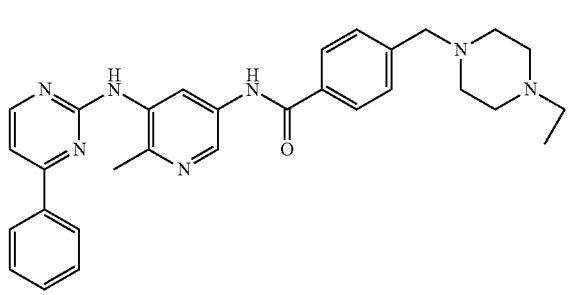 [SMILES: CCN1CCN(Cc2ccc(C(=O)Nc3cnc(C)c(Nc4nccc(-c5ccccc5)n4)c3)cc2)CC1]

in free or salt form.

3. The compound according to claim 1 wherein the compound of formula (Q) is

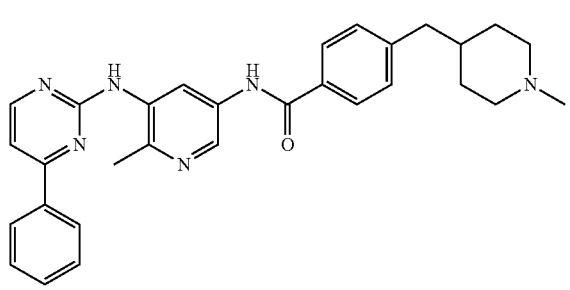

in free or salt form.

4. The compound according to claim 1 wherein the compound of formula (Q) is

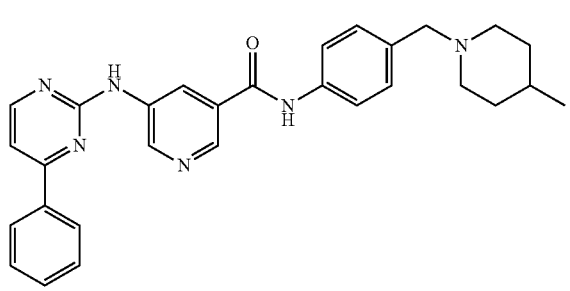 [SMILES: CC1CCN(Cc2ccc(NC(=O)c3cncc(Nc4nccc(-c5ccccc5)n4)c3)cc2)CC1]

in free or salt form.

5. The compound according to claim 1 wherein the compound of formula (Q) is:

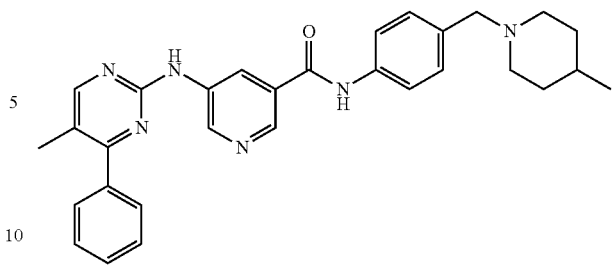

in free or salt form.

6. The compound according to claim 1 wherein the compound of formula (Q) is:

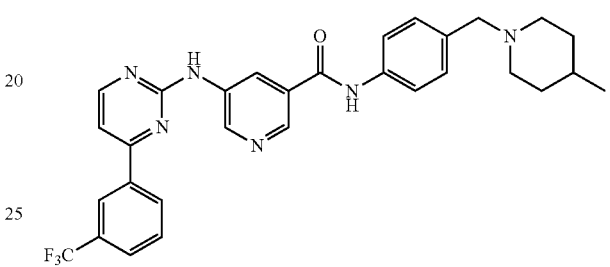

in free or salt form.

7. The compound according to claim 1 wherein the compound of formula (Q) is:

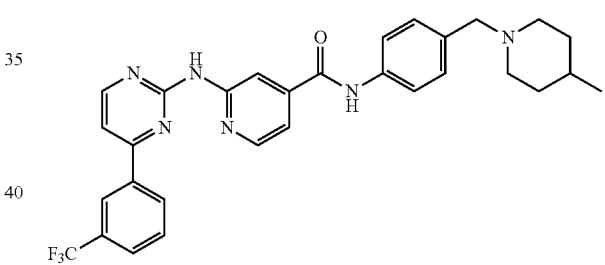

in free or salt form.

8. A compound of formula (I):

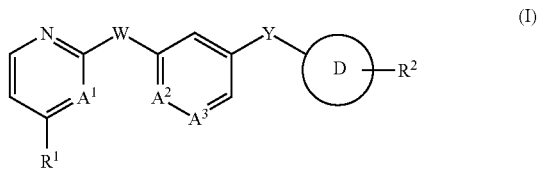

(I)

in free or salt form, wherein:
A$^1$ is CH or N;
A$^2$ and A$^3$ are independently CH or N, wherein at least one of A$^2$ and A$^3$ must be N; and wherein when A$^2$ or A$^3$ is C, it is optionally substituted with halo, methyl, methoxy, or trifluoromethyl;
W is —O— or —N(C$_{0-6}$alkyl)-;
Y is —NHCO—, —CONH—, —NHSO$_2$—, —NHCONH—, or —NHCH$_2$—;
D is a 5 or 6 membered aryl, hetaryl or hetcyclic ring having at least one N, S, or O ring atom, or a C ring atom forming an oxo (C=O) moiety;

R[1] is phenyl; optionally substituted except at the ortho position of the phenyl with 1-6 halo, $C_{1-6}$alkoxy, $C_{1-6}$alkyl, or trifluoromethyl substituents; wherein the ortho phenyl position is unsubstituted; and R[2] is hetcyclyl($C_{0-4}$alkyl)-, optionally substituted with $C_{1-6}$alkyl.

9. A pharmaceutical composition which comprises a compound, in free or pharmaceutically acceptable salt form, according to claim 1, in association with a pharmaceutically-acceptable diluent or carrier.

10. A method of treatment of a disease or disorder characterized as a neurodegenerative disease comprising administering an effective amount of the compound according to claim 1, in free or pharmaceutically acceptable salt form, to a patient in need thereof.

11. The method according to claim 10, wherein the disease or disorder characterized as a neurodegenerative disease is selected from the group consisting of: Alzheimer's disease, progressive supranuclear palsy, Down Syndrome, dementia, amyloid neuropathies, brain inflammation, nerve and brain trauma, vascular amyloidosis, cerebral hemorrhage with amyloidosis, Parkinson's disease, Huntington's disease, and prion disease.

12. The method according to claim 10, wherein said disease or disorder is Alzheimer's disease.

13. A method of treatment of a disease or disorder characterized as hyperproliferative comprising administering the compound according to claim 1, in free or pharmaceutically acceptable salt form, to a patient in need thereof.

14. A method of treatment, control and management of diseases characterized by accumulation of abnormal protein aggregates comprising administering an effective amount of the compound according to claim 1, in free or pharmaceutically acceptable salt form, to a patient in need thereof.

15. The method of claim 14, wherein said disease is characterized by accumulation of abnormal protein aggregates in the brain.

16. A method of treatment, control and management of vascular, neurological, or neurodegenerative disorders related to the abnormal expression or accumulation of tau or amyloid proteins, comprising administering an effective amount of the compound according to claim 1, in free or pharmaceutically acceptable salt form, to a patient in need thereof.

17. The method of claim 14, wherein the disease or disorder characterized by the accumulation of abnormal protein aggregates is selected from the group consisting of: amyloid plaques, neurofibrillary tangles, or precipitates of tau or amyloid proteins.

18. A method of treatment of disease or disorders characterized as cancers of the brain or central nervous system, comprising administering an effective amount of the compound according to claim 1, in a free or pharmaceutically acceptable salt form, to a patient in need thereof.

19. The method of claim 13, wherein the disease or disorder characterized as hyperproliferative is selected from the group consisting of: astrocytoma, medulloblastoma, oligdendroglioma, glioblastoma, glioma, ependymoma, meningioma, sarcoma, germ cell tumor, pinealoma, craniopharyngioma, and pituitary adenoma.

20. A method of treatment of a disease or disorder characterized by dysfunctional kinase expression or kinase activity comprising administering an effective amount of the compound according to claim 1, in free or pharmaceutically acceptable salt form, to a patient in need thereof.

21. The method of claim 20, wherein the disease or disorder characterized by dysfunctional kinase expression or kinase activity is selected from the following group of kinases consisting of: c-Abl, BCR-Abl, ARG, c-Src, c-Kit, FAK, Trk, EGFR, VEGFR, Tie-2, c-Met, FGFR-1, Flt-1, Her-2, c-Raf, PDGFR, PDGFR-beta, MAPK, PKA, PKC, PKCα, PKCδ, CDK5, GSK-3, and JNK.

22. The method of claim 10, wherein the neurodegenerative disease or disorder is a memory or cognitive disorder.

23. The method of claim 17, wherein the disease or disorder is Alzheimer's disease and the abnormal protein aggregates are amyloid plaques.

24. The compound according to claim 1, wherein W is —NH—, in free or salt form.

25. The compound according to claim 1, wherein A[1] is —N—, in free or salt form.

26. The compound according to claim 1, wherein A[2] is —C—optionally substituted with methyl, in free or salt form.

27. The compound according to claim 1, wherein A[3] is —N—, in free or salt form.

28. The compound according to claim 1, wherein Y is —NHCO—, in free or salt form.

29. The compound according to claim 1, wherein D is aryl, in free or salt form.

30. The compound according to claim 1, wherein D is phenyl, in free or salt form.

31. The compound according to claim 1, wherein R[1] is phenyl optionally substituted except at the ortho position of the phenyl with 1-6 halo, $C_{1-6}$alkoxy, $C_{1-6}$alkyl, or triflouromethyl, in free or salt form.

32. The compound according to claim 1, wherein R[1] is phenyl, in free or salt form.

33. The compound according to claim 1, wherein R[2] is piperidin-1-yl($C_{0-4}$alkyl)-, piperidin-4-yl($C_{0-4}$alkyl)-, piperazin-1-yl($C_{0-4}$alkyl)- or piperazin-4-yl($C_{0-4}$alkyl)-, optionally substituted with $C_{1-6}$alkyl, in free or salt form.

34. The compound according to claim 1, wherein R[2] is piperidin-1-ylmethyl, 4-methylpiperidin-1-ylmethyl, N-methylpiperidin-4-ylmethyl, piperazin-1-ylmethyl, 4-methylpiperazin-1-ylmethyl or ethylpiperazin-1-ylmethyl, in free or salt form.

35. The compound according to claim 8, wherein the compound is a compound of formula (I)

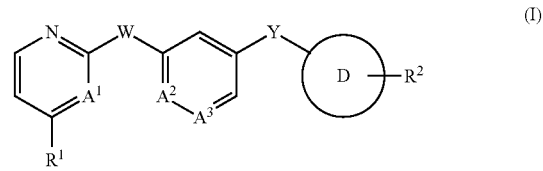

in free or salt form, wherein:
A[1] is N; A[2] and A[3] are independently CH or N, wherein at least one of A[2] and A[3] must be N; and wherein when A[2] or A[3] is C, it is optionally substituted with halo, methyl, methoxy, or trifluoromethyl;
W is —N($C_{0-6}$alkyl)-;
Y is —NHCO—, or —CONH—;
D is a 5 or 6 membered aryl, hetaryl or hetcyclic ring having at least one N, S, or O ring atom;
R[1] is phenyl;
R[2] is hetcyclyl($C_{0-4}$alkyl)-, optionally substituted with $C_{1-6}$alkyl.

36. The compound according to claim 35, wherein A[2] is —C—, optionally substituted with methyl, in free or salt form.

37. The compound according to claim 35, wherein $A^3$ is —N—, in free or salt form.

38. The compound according to claim 35, wherein W is —NH—, in free or salt form.

39. The compound according to claim 35, wherein Y is —NHCO—, in free or salt form.

40. The compound according to claim 35, wherein D is aryl, in free or salt form.

41. The compound according to claim 35, wherein D is phenyl, in free or salt form.

42. The compound according to claim 35, wherein $R^2$ is piperidin-1-yl($C_{0-4}$alkyl)-, piperidin-4-yl($C_{0-4}$alkyl)-, piperazin-1-yl($C_{0-4}$alkyl)- or piperazin-4-yl($C_{0-4}$alkyl)-, optionally substituted with $C_{1-6}$alkyl, in free or salt form.

43. The compound according to claim 35, wherein $R^2$ is piperidin-1-ylmethyl, 4-methylpiperidin-1-ylmethyl, N-methylpiperidin-4-ylmethyl, piperazin-1-ylmethyl, 4-methylpiperazin-1-ylmethyl or ethylpiperazin-1-ylmethyl, in free or salt form.

\* \* \* \* \*